United States Patent [19]

Dorman

[11] Patent Number: 4,657,536
[45] Date of Patent: Apr. 14, 1987

[54] CHECK VALVE CATHETER

[75] Inventor: Frank D. Dorman, Minneapolis, Minn.

[73] Assignee: Regents of the University of Minnesota, Minneapolis, Minn.

[21] Appl. No.: 245,379

[22] Filed: Mar. 19, 1981

Related U.S. Application Data

[63] Continuation-in-part of Ser. No. 29,640, Jul. 13, 1979, abandoned.

[51] Int. Cl.⁴ ............................................. A61M 25/00
[52] U.S. Cl. ....................................... 604/247; 604/9; 137/860
[58] Field of Search ....... 128/214 R, 274, 348-350 V, 128/1 D, 656-658; 137/853, 860; 604/247

[56] References Cited

U.S. PATENT DOCUMENTS

| | | | |
|---|---|---|---|
| 3,288,901 | 11/1966 | Clark | 128/349 R X |
| 3,384,113 | 5/1968 | Pennisi | 137/853 |
| 3,731,681 | 5/1973 | Dorman | 128/214 F |
| 3,885,561 | 5/1975 | Cami | 128/214 R |
| 3,888,249 | 6/1975 | Spencer | 128/214 R |
| 3,995,617 | 12/1976 | Watkins et al. | 128/1 D |
| 4,063,555 | 12/1977 | Ulinder | 128/214 R |

Primary Examiner—Dalton L. Truluck
Attorney, Agent, or Firm—Burd, Bartz & Gutenkauf

[57] ABSTRACT

A catheter having a tip which is resistant to plugging by blood components or other body fluids when used as a long term implant within a living body. A check valve is incorporated in the tip that is exposed to the blood stream or other body fluids. The central bore within the catheter is closed at its downstream end. A cross bore or port is provided immediately upstream from the closed end. This cross bore is covered by a thin elastic sleeve to create a check valve. The pressure developed by injected infusate through the catheter opens the valve against the elastic force of the outer sleeve. Fluids cannot enter the catheter either by diffusion against the high velocity exit flow or by suction applied to the proximal end of the catheter.

8 Claims, 4 Drawing Figures

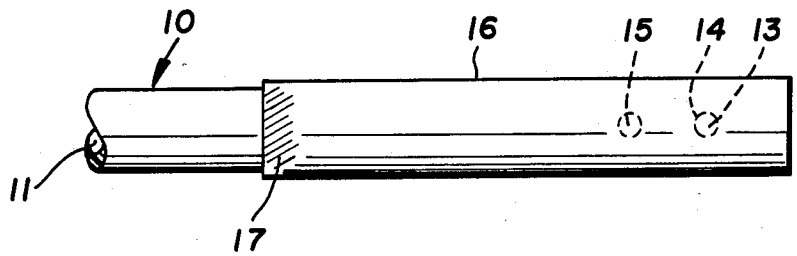
FIG.1
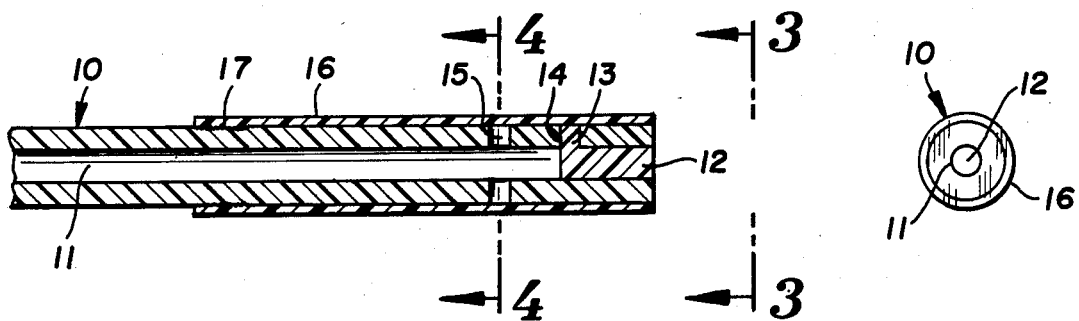
FIG.2  FIG.3
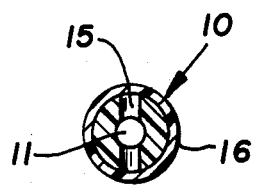
FIG.4

CHECK VALVE CATHETER

The invention described herein was made in the course of work under a grant or award from the Department of Health, Education and Welfare.

This application is a continuation-in-part of application Ser. No. 29,640, filed Apr. 13, 1979, and now abandoned.

BACKGROUND OF THE INVENTION

1. Field of the Invention

This invention is directed to a catheter intended for implantation within a living body for long term operation. The catheter is intended for use, for example, with the implantable infusion pump or artificial gland described in U.S. Pat. No. 3,731,681, or with other implanted injection ports for drug delivery to internal organs or sites not accessible by direct needle puncture.

2. The Prior Art

The major problems with long term catheterization of a blood vessel are infection at the skin puncture point and clotting in the catheter lumen. Only in cases where the flow rate of infusate is very high, or if an anti-coagulant is being infused, does the catheter tip remain open for a long term. In applications such as insulin infusion, the flow rates are very low, and back diffusion of blood components can result in clots or plugs forming inside the lumen of the catheter. This limits the useful lifetime of the indwelling catheter in many instances to only three to four months.

In the case of use of an implanted infusion pump such as that of aforesaid U.S. Pat. No. 3,731,681, a further complication exists in that the catheter does not always have a forward flow. For example, when the pump is being filled, it is possible to momentarily generate suction which pulls blood retrograde back into the catheter and this blood inevitably clots. Also, changes in blood pressure may cause a fluctuating pressure at the tip of the catheter and can induce backward flow up the catheter. The cyclic pressure pumps fluid along the wall where the velocity is low. The catheters are always designed with a small exit hole to keep the velocity of the infusate as high as possible. However, this also has danger in that the cross section is very small and can be easily plugged. The plug can come from material that diffuses upstream from the blood or from small particles which come downstream out of the pump itself. If the hole is made very small to obtain high velocity, it is difficult to keep it from plugging due to particulates in the infusate. The ideal catheter is one in which it is not necessary to maintain a fixed flow rate to keep it open. Therefore, the catheter flow rate may be allowed to go to zero for long periods of time. The catheter should also be able to pass particles that come downstream with the infusate without plugging the tip. In order to resist back diffusion, the exit hole should be as small as possible to maintain a critically high exit velocity. The catheter of the present invention incorporates these desirable features and overcomes the shortcomings of prior art devices.

SUMMARY OF THE INVENTION

Broadly stated, the present invention is directed to a long term implantable catheter having a check valve tip for unidirectional flow. The catheter is an elongated relatively thick walled tubular member having a central bore. The bore is open at the upstream end to receive infusate and is closed at the bottom end, as by a plug. At least one cross bore or port is provided in the wall of the tubular member communicating with the central bore and located upstream from and closely adjacent to the closed catheter end. A thin elastic sleeve surrounds the tubular member in squeezing engagement. This sleeve covers the port. The sleeve is tightly secured against dislodgment from the tubular member, as by adhesive bonding or the like, upstream from the port. The remainder of the sleeve engages the outer wall of the tubular member in squeezing but unbonded relation. The pressure of infusate introduced through the catheter is sufficient to expand the elastic sleeve to permit fluid to pass from the port through the space created in the annular interface between the inside sleeve wall and outside catheter tip wall.

BRIEF DESCRIPTION OF THE DRAWINGS

The invention is illustrated in the accompanying drawings in which corresponding parts are identified by the same numerals and in which:

FIG. 1 is a side elevation of one form of check valve catheter tip according to the present invention;

FIG. 2 is a side elevation in section of the catheter tip shown rotated 90° from FIG. 1;

FIG. 3 is an end elevation of the catheter tip; and

FIG. 4 is a transverse section through the ports taken on the line 4—4 of FIG. 2 and in the direction of the arrows.

DETAILED DESCRIPTION OF THE PREFERRED EMBODIMENT

Referring now to the drawings, there is shown a relatively thick walled tubular catheter, indicated generally at 10, having a central bore 11 throughout its length. The catheter tube may be formed from any of a large number of flexible inert non-toxic bio-compatible rubber or synthetic rubber-like materials. A preferred material is a standard radio-opaque barium-filled silicone rubber which, apart from having excellent catheter properties, may be located using fluorscopic techniques once implanted. Likewise, the catheter tube may have widely varying dimensions dependent upon the particular application to which it is to be put. One exemplary catheter tube is 0.093 inch (0.236 cm) outside diameter having a central bore of 0.016 inch (0.041 cm) diameter. It may be of whatever length required to reach the desired infusion site.

The upstream end of bore 11 is open to receive fluid to be infused. The downstream end is closed, as by a short plug 12. As illustrated, plug 12 has a radial spur 13 extending into a transverse opening 14 in the wall of the catheter tip. While plug 12 may likewise be formed from any one of a number of biologically compatible materials, a preferred material is medical grade silastic adhesive.

One convenient method of forming plug 12 is as follows: Hole 14 is bored through one wall of the catheter a short distance, such as 5/16 inch (0.794 cm) from the end. The catheter tube is clamped off upstream from hole 14 and a vacuum is applied to the open bore. Silastic adhesive paste is applied over hole 14 and drawn through the hole out through the end of the tube, thus forming plug 12. The excess paste is wiped from the outer surface and the plug is cured to insure a firm leak-proof bond between the plug and the wall of bore 11. The integrity of the plug seal is preferably tested by application of forward bias pressures of about 50 psig (3.5 Kg/sq. cm) for 5 minutes.

The plugged catheter tip is then provided with a cross bore 15 to provide one or more ports from the catheter. Port 15 is located immediately upstream from plug 12, for example, about 3/16 inch (0.476 cm) in the exemplary catheter. The diameter of the exit port may be approximately the same diameter as the catheter bore.

A thin-walled elastic sleeve 16 is applied over the catheter tip so as to cover port 15. In the exemplary catheter, sleeve 16 may be about 1.25 inches (3.175 cm) long. Dependent upon the elasticity and strength of the material, it should be about 0.0005 to 0.01 inch (0.0013 to 0.025 cm) thick. The upstream end of sleeve 16 is sealed to the catheter tube by means of an adhesive bond extending around the periphery of the catheter tube.

Sleeve or sheath 16 is made undersized, approximately 5 to 30 percent, again dependent upon the elasticity and strength of the material, to generate a fixed compression at the end of the catheter. As an example, using the exemplary catheter having an outside diameter of 0.093 inch (0.236 cm), a sleeve of inside diameter of 0.0748 inch (0.190 cm) provides a squeeze factor of about 24.3 percent. That is, the outside catheter diameter (0.093 inch=0.236 cm) divided by the inside sleeve diameter (0.0748 inch=0.190 cm) equals 1.243. This value minus 1 and multiplied by 100 equals a 24.3 percent squeeze factor.

Sleeve 16 may likewise be formed from a number of different biologically compatible materials having the requisite elasticity. A preferred material is polyurethane polymer (Biomer). The forward opening pressure of the check valve catheter tip is a function of both the thickness of the sleeve and the squeeze factor, both of which may be controlled. The sleeve is desirably formed by dipping of a cylindrical mandrel of appropriate diameter into a solution of the polymer. The thickness of the resulting sleeve is directly proportional to the concentration of solvent in the polymer (viscosity), which rapidly changes with time as a function of exposure to air (humidity, temperature, etc.) and probably many other factors. Good results have been obtained using fresh unopened Biomer polyurethane in mixtures of 3 parts polymer to 1 part of N-N-dimethylacetamide thinner.

The urethane sleeve is desirably formed by first dipping the previously cleaned and dried mandrel into the polymer solvent and then quickly into the polymer solution itself. Once into the polymer solution, the solvent diffuses away from the mandrel surface carrying with it any air or other impurities, leaving a uniform coat. If the polymer solution contains entrained air, this is preferably purged from the solution by application of vacuum prior to use. The mandrel is desirably dipped into the solution with a slow twisting motion and then retracted with the same twisting motion. To form the exemplary sleeve which is 1.25 inches (3.175 cm) long, the mandrel is dipped into the solution about 1.5 inches (3.8 cm) and retracted at a rate of about ⅔ inch (1.69 cm) per minute. After the mandrel is free of the solution, it is rested in a vertical position on a drying stand. The force of gravity pulls off excess polymer, leaving a uniform coat varying from about 0.0015 inch (0.0038 cm) at the top to about 0.002 inch (0.0051 cm) at the bottom. The sleeve is then cured by heating at about 120° F. (49° C.) for about 36 hours.

Once cured, the sleeve is inspected for impurities, air bubbles, dust, etc. in the surface. It is trimmed to useful length and expanded off the mandrel by soaking in trichloroethylene for about 15 to 20 minutes. This expands the sleeve to about one and one-half times its normal diameter and about 10 percent in length. This permits easy transfer to the catheter tip. As the solvent evaporates, the cured sleeve returns to its original dimensions in tight squeezing engagement with the outer wall of the catheter tip. The sleeve is sealed to the wall of the catheter tip, as for example, by rolling the upstream end of the sleeve back a short distance, applying a biologically compatible adhesive, such as silastic adhesive, to the catheter, quickly rolling the sleeve back over the adhesive and curing to form a permanent bond. The end of the catheter tip is preferably trimmed in a sharp cut.

Although polyurethane is a preferred material for formation of sleeve 16, other inert non-toxic rubber or synthetic rubber-like materials which are compatible with body fluids and which have the requisite elasticity can be used instead. When available, preformed tubular material may be used to form the sleeve.

The length of sleeve needed is based on the fabrication method and on the need to maintain a pressure seal on the catheter downstream from the side exit port. Bending or contact with the blood vessel walls can cause the sleeve to slide back along the catheter a small amount so a minimum length of sleeve is necessary to prevent uncovering of the exit port by these actions. Preferably the side exit port is located about 2 to 10 catheter diameters upstream from the closed end. The sleeve length is at least 2 to 10 catheter diameters long, dependent upon the location of the port, plus additional length sufficient to secure the upstream end of the sleeve to the catheter without the adhesive bond obstructing the port. The downstream end of the sleeve and the closed end of the catheter tip terminate in a plane transverse to the longitudinal axis of the catheter to provide a high velocity jet port.

In use, the drug or other material to be infused is introduced into the end of the catheter under pressure, such as might be applied by the pump of the aforesaid U.S. Pat. No. 3,731,681. The pressure of the fluid exiting from port 15 is sufficient to overcome the compressive force of sleeve 16 to cause the fluid to flow along the interface between the outside wall of the catheter tip and inside wall of the sleeve. The compressive force of the sleeve prevents back-flow into the catheter. Even where the infusate is introduced at a very low flow rate, such as insulin at the rate of approximately 1 cc per day, the flow rate at the exit slit at the end of the catheter tip at the interface between the sleeve and tip wall where the insulin enters the bloodstream is at a sufficiently high velocity to inhibit significant back-diffusion of blood components into the interface channel. Even if there is a small rate of buildup of deposit in this channel, the elastic nature of the sleeve is such that the sleeve may expand to permit continued flow with approximately the same pressure drop. The fluid channel at the interface may also move radially around the catheter until it finds a clean area which has been previously closed due to the elastic force and thus establish a new channel.

Ordinarily the flow rate is along one channel extending along the interface from the cross bore port to the free end of the catheter tip. Only when the fluid is introduced at very high flow rates will the sleeve expand to allow flow completely around the annular exit. This gives a very large effective exit cross section while at the same time maintaining a high exit velocity. Where the infusate may contain particles which might otherwise clog the catheter, the sheath either expands to allow the particle to pass through or traps the particle to allow flow around it. The catheter tip is thus unpluggable from both directions due to the expandability of the sleeve. Negative pressures as great as $-20$ psi ($-1.4$ Kg/sq. cm) ($P_{in}-P_{out}$) have been witnessed without failure. These are pressures far beyond those that would be expected in clinical situations.

Although intended primarily for use with an implantable pump or artificial gland, such as described in aforesaid U.S. Pat. No. 3,731,681, the catheter may also be used with only an implanted septum. For example, a catheter is surgically implanted in a difficult-to-place location, such as a vein or artery going into some internal organ that is not accessible by needle puncture from the surface of the body. After this catheter has been implanted and a puncture septum is placed at a convenient location under the skin, the internal organ can be perfused with any infusate by simple puncture of the readily accessible external puncture point. The use of this technique avoids the necessity for passing the ctheter through the skin and the chronic problems associated therewith.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A check valve catheter tip for unidirectional high velocity jet flow for an infusion catheter for implantation within a living body for long-time residence therein for the low flow rate infusion of a liquid drug into the body, said catheter tip comprising:
   (A) an elongated relatively thick-walled, small diameter, bio-compatible, flexible tubular member,
   (B) a central bore in said member, said bore being open at the upstream end and closed at the downstream end,
   (C) a radial hole in said tubular member communicating with the bore adjacent to the closed end,
   (D) a plug in the closed end of the bore in fluid-tight sealing engagement with the bore wall, said plug having a radial spur engaging said radial hole in the tubular member in fluid-tight sealing engagement,
   (E) at least one port in the wall of the tubular member communicating with said bore, said port being located upstream from said plug and closely adjacent thereto,
   (F) a thin elastic sleeve surrounding said tubular member in squeezing engagement therewith, the diameter of said sleeve being about 5 to 30 percent less than the outside diameter of said tubular member, said sleeve covering said port and being relatively long compared to the diameter of the catheter to provide a relatively long flow channel, and
   (G) means securing the upstream end of said sleeve to the tubular member upstream from the port, the downstream end of the sleeve and the closed end of the catheter tip terminating in a plane transverse to the longitudinal axis of the catheter to provide a high velocity jet port.

2. A catheter tip according to claim 1 further characterized in that said thin elastic sleeve is between about 0.0005 and 0.01 inch (0.0013 and 0.025 cm) in thickness.

3. A catheter tip according to claim 1 wherein said means for securing the sleeve to the tubular member is an adhesive bond between the inside wall of the sleeve and the outside wall of the tubular member.

4. A catheter tip according to claim 1 wherein said tubular member is composed of silicone rubber and said sleeve is composed of polyurethane.

5. A catheter tip according to claim 4 wherein said silicone tubular member is barium-filled and radioopaque.

6. A check valve catheter tip for unidirectional flow comprising:
   (A) an elongated relatively thick-walled tubular member,
   (B) a central bore in said member, said bore being open at the upstream end and closed at the downstream end,
   (C) a plug in fluid-tight sealing engagement with the bore wall at the closed end of said bore,
   (D) a radial hole in said tubular member communicating with the bore and a radial spur on said plug engaging said hole in fluid-tight sealing engagement,
   (E) at least one port in the wall of the tubular member communicating with said bore, said port being located upstream from said closed end of the tubular member and closely adjacent thereto,
   (F) a thin elastic sleeve surrounding said tubular member in squeezing engagement therewith, said sleeve covering said port, and
   (G) means securing said sleeve to the tubular member upstream from the port.

7. A catheter tip according to claim 6 wherein the original inside diameter of said sleeve is about 5 to 30 percent less than the outside diameter of said tubular member.

8. A catheter tip according to claim 6 wherein the closed end of the catheter tip and the end of the sleeve terminate in a plane transverse to the longitudinal axis of the catheter to provide a high velocity annular jet port.

* * * * *